United States Patent [19]

Scapinelli

[11] Patent Number: 4,591,500

[45] Date of Patent: May 27, 1986

[54] TABLET HAVING THE SHAPE OF A CAPSULE, PROCESS AND DEVICE FOR ITS PREPARATION

[75] Inventor: Bruno Scapinelli, Lamorlaye, France

[73] Assignee: Microencapsulation S.A., Chiasso, Switzerland

[21] Appl. No.: 656,968

[22] Filed: Oct. 2, 1984

Related U.S. Application Data

[62] Division of Ser. No. 488,457, Apr. 25, 1983, abandoned.

[51] Int. Cl.$^4$ ............ A61K 9/20; A61K 9/44
[52] U.S. Cl. .................. 424/15; 425/352; D28/1; D28/2
[58] Field of Search ................................ 424/15

[56] References Cited

U.S. PATENT DOCUMENTS

| | | | |
|---|---|---|---|
| 3,860,733 | 1/1975 | Morse et al. | 424/35 |
| 3,952,096 | 4/1976 | Godfrey et al. | 424/156 |
| 4,097,606 | 6/1978 | Chavkin et al. | 424/324 |
| 4,140,755 | 2/1979 | Sheth et al. | 424/19 |
| 4,167,558 | 9/1979 | Sheth et al. | 424/22 |
| 4,308,251 | 12/1981 | Dunn et al. | 424/19 |
| 4,353,887 | 10/1982 | Hess et al. | 424/15 |
| 4,369,172 | 1/1983 | Schor et al. | 424/19 |
| 4,374,082 | 2/1983 | Hochschild | 264/129 |
| 4,376,111 | 3/1983 | Tovey | 424/15 |
| 4,389,393 | 6/1983 | Schor et al. | 424/19 |

OTHER PUBLICATIONS

Little et al., Tablet Making 2nd ed. (1963) Northern Publ. Co. Liverpool, England pp. 4–13, 31–33, 42–43, 52–53, 68–81, 108–111.

Remington's Pharmaceutical Sciences, 14th ed. (1970) p. 1660.

*Primary Examiner*—Shep K. Rose
*Attorney, Agent, or Firm*—Gordon W. Hueschen

[57] ABSTRACT

A tablet having the shape of a gelatine capsule avoids the swallowing and digestion drawbacks of said capsules and consists of a blend of one or more excipients and granules of one or more active substances, said blend being compressed along the longitudinal direction, i.e. at both heads or ogives, so as not to damage integrity of granules, in a suitable molding device provided with at least an upper die and a lower die. The invention relates also to such a device as well as the process of obtaining said tablet.

3 Claims, 3 Drawing Figures

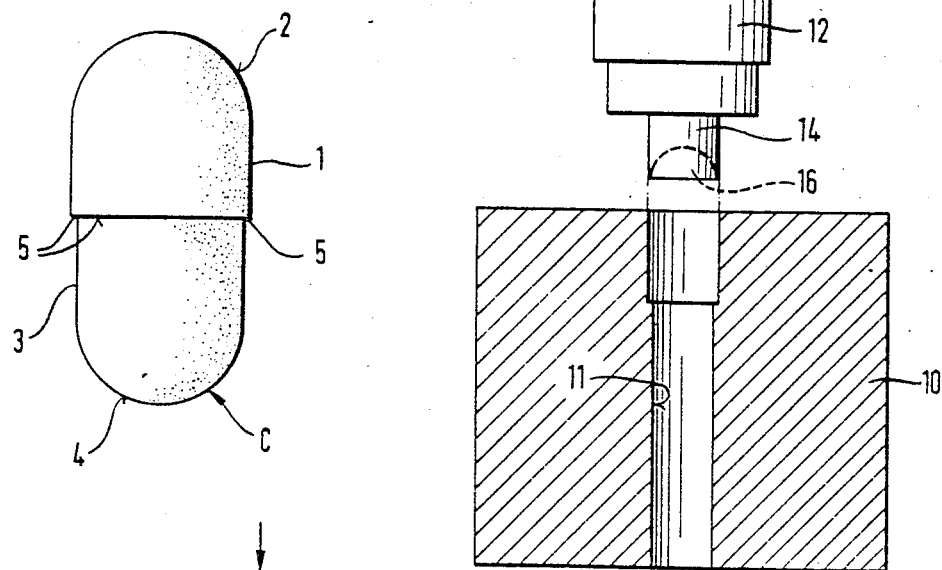
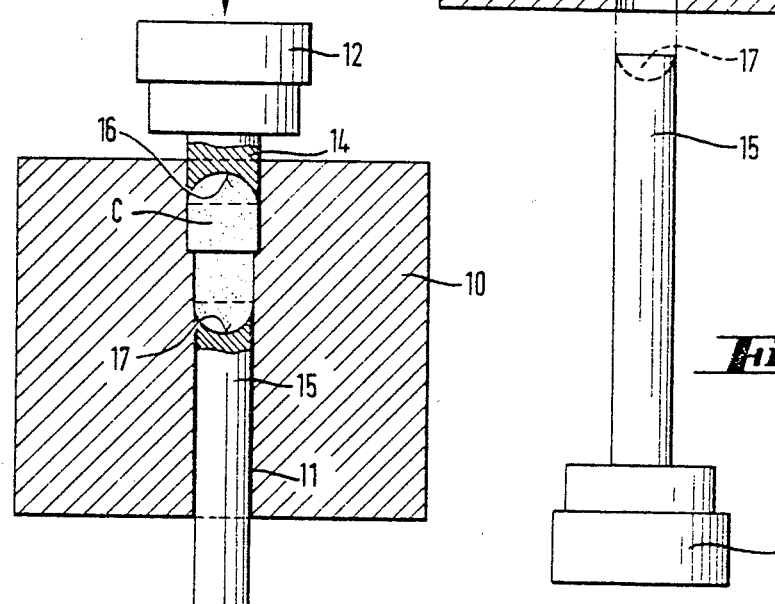
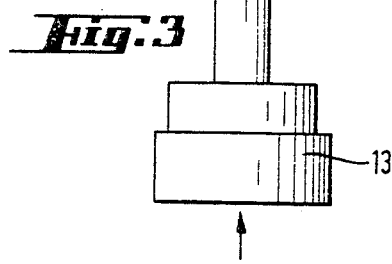

TABLET HAVING THE SHAPE OF A CAPSULE, PROCESS AND DEVICE FOR ITS PREPARATION

This is a division of application Ser. No. 488,457, filed Apr. 25, 1983, aband.

BACKGROUND OF THE INVENTION

1. Field of the Invention

The present invention relates to a tablet having the shape of a capsule, as well as a process and a device to carry out preparation of said tablets.

2. State of the Art

It is well known that many pharmaceutical compositions, more particularly those in which it is necessary to mask taste and/or odor, or where the composition should reach intact stomach or intestine like drugs with sustained or retarded action, are prepared for administration in the form of capsules, comprising an outer envelope, which can be either hard or soft and generally made of gelatine or similar neutral materials, containing the granules or pellets of active substance or raw material.

However these capsules are rather big and many persons have difficulties to swallow them, the neutral material of the envelope gives rise to troubles either in the stomach or in the intestine, and their manufacture and preparation requires several operations and apparatuses, making said capsules relatively expensive in comparison with other simpler forms of conventional administration.

On the other hand it would be impossible to make a normal tablet containing granules or microgranules of active substance, more particularly those with sustained or retarded action which must not be damaged in order not to alter time and manner of releasing the active substance, because the conventional tabletting machines, exerting a strong compression on a wide and short discoid, would destroy integrity of most granules or microgranules.

SUMMARY OF THE INVENTION

The present invention solves this problem, highly felt in the pharmaceutical field, and provides for a tablet having the feature of the shape of a capsule, consisting of one or more neutral excipients incorporating the granules or microgranules of one or more active substances, perfectly keeping their integrity, so as not to alter time and manner of the action of active substance enclosed therein.

It is clear that both excipients (such as starch) and raw materials may be all those desired and suitable, as there is neither limitation nor exclusion in this respect.

The tablet according to the present invention may therefore replace the conventional gelatine capsules, and has further advantages in comparison with them, because it may be easily swallowed and releases immediately the granules once it arrives in the stomach or in the intestine when it is prepared with gastroresistant excipients.

The process allowing to obtain this result, that is to say to produce a tablet having the shape of a capsule by keeping integrity of the granules, is characterized by the fact that the blend of neutral excipient incorporating the granules of active substance, is compressed in the longitudinal direction (instead of the width like in the conventional tabletting machines), thus exerting pressure on the two tablet heads, i.e. on small surfaces in respect to the tablet mass, so that the granules enclosed in said mass do not undergo any such stress as to alter their chemical and physical characteristics.

Another very important advantage of the tablet having the shape of a capsule according to the present invention, which however is optional and not limiting the broad scope of the invention, is that this tablet may be divided into portions, so that administration of the drug may also be divided into several doses, which is obviously impossible with capsules.

Preferably, though not necessarily, the shape of the tablet according to the present invention reproduces exactly the form of the gelatine capsules, that as it is well known consist of two semicapsules of which one is inserted into the other, so that the division point of the tablet in two halves is represented by the step representing the connection point of the two semicapsules, and the quantity of active substance in each tablet half will be the same and therefore one can be sure to administer perfectly equal hemidoses.

The device for carrying out the above process and preparing in practice the tablets having the shape of a capsule according to the present invention is characterized by a mold comprising at least a vertical chamber, in which the blend of suitable excipient and granules of active substance is introduced and compressed between an upper die and a lower die, each of them having the end or head acting on the blend in the form of an ogive matching the form of the corresponding head of the tablet in the shape of a capsule to be obtained. It is clear that for a mass production the mold will have a set of tablet forming chambers with the same number of upper dies and lower dies which will be actuated at the same time or sequentially, and the device will be provided with all the mechanisms and controls being normal in any machine for mass production of articles.

BRIEF DESCRIPTION OF THE DRAWING

As a non limiting example of the invention, a tablet having the shape of a capsule and a device for its production are shown in the accompanying illustrative drawing, in which:

FIG. 1 is a plan view of a tablet having the shape of a capsule according to the present invention;

FIG. 2 is a diagrammatic sectional view of the device for the production of the tablet shown in FIG. 1, in the position with open dies; and FIG. 3 is a diagrammatic sectional view of the same device of FIG. 2, but in the tablet forming position with closed dies.

DETAILED DESCRIPTION OF THE PREFERRED EMBODIMENTS

With reference now to the accompanying drawing, FIG. 1 shows a tablet having the shape of a capsule according to the present invention, reproducing exactly the shape of the gelatine capsules, thus comprising an upper semicapsule 1 with its hemispherical head or ogive 2 and a lower semicapsule 3 with its hemispherical head or ogive 4, defined by the separation line or step 5, along which the capsule may possibly be divided in two halves. As already stated, it is however to be understood that the tablet could also be made without step 5 or have more than one step so as to be allowed to divide it into a greater number of doses.

Turning now to FIGS. 2 and 3, the device for producing said tablets consists of a mold 10 having at least one vertical chamber 11 (but preferably a set of chambers arranged in an array, i.e. rows, lines or circles), in which the blend is introduced, comprised of one or more suitable excipients (e.g. starch) and granules of one or more active substances, said blend being compressed between an upper die 12 and a lower die 13, each of them having at the end or head 14 or 15 acting on the blend, the shape or form 16 or 17 of the corresponding hemispherical heads or ogive 2 or 4 of the tablet having the shape of a capsule C which is thus being formed by compression between said dies, exerted in the longitudinal or axial direction of the tablet, on its two heads or ogives 2 and 4, therefore without damaging the granules or pellets enclosed in the blend.

From the foregoing it is therefore clear that objects and advantages of the invention were fully met, and many variations, modifications, additions and/or substitutions of elements may be resorted to the tablet (which may undergo all the subsequent finishing and/or packaging operations which may be required) as well as to the process and the device of the invention, without departing however from its spirit and scope, as it is also defined in the appended claims.

I claim:

1. Pharmaceutical tablet, consisting essentially of a blend of one or more excipients and one or more active substances in the form of granules or microgranules, compressed into the shape of a capsule comprising two semicapsules, each provided with a head or ogive, and having a step at the juncture between the two semicapsules which together form the tablet.

2. Tablet according to claim 1, wherein the tablet may be divided into portions determined by lines along which the tablet may be severed, said lines including the step which is present at the connecting point or juncture between the two semicapsules which together form the tablet.

3. Tablet according to claim 2, wherein the tablet may be divided into two halves which may be severed along the said step.

* * * * *

Notice of Adverse Decision in Interference

In Interference No. 101,939, involving Patent No. 4,591,500, B. Scapinelli, TABLET HAVING THE SHAPE OF A CAPSULE, PROCESS AND DEVICE FOR ITS PREPARATION, final judgment adverse to the patentee was rendered Mar. 21, 1989, as to claims 1-3.

[*Official Gazette May 30, 1989* ]